United States Patent
Newman et al.

(10) Patent No.: US 6,838,095 B2
(45) Date of Patent: Jan. 4, 2005

(54) IONIC SILVER COMPLEX

(75) Inventors: Ira Jay Newman, 2805 E. Oakland Park Blvd., #600, Fort Lauderdale, FL (US) 33306; David Washburn, West Palm Beach, FL (US)

(73) Assignee: Ira Jay Newman, Fort Lauderdale, FL (US)

( * ) Notice: Subject to any disclaimer, the term of this patent is extended or adjusted under 35 U.S.C. 154(b) by 0 days.

(21) Appl. No.: 10/383,345

(22) Filed: Mar. 7, 2003

(65) Prior Publication Data

US 2003/0147970 A1 Aug. 7, 2003

Related U.S. Application Data

(63) Continuation of application No. 10/175,260, filed on Jun. 18, 2002, now abandoned, which is a continuation of application No. 09/796,242, filed on Feb. 28, 2001, now abandoned, which is a continuation of application No. 09/435,158, filed on Nov. 5, 1999, now abandoned.

(60) Provisional application No. 60/107,710, filed on Nov. 9, 1998.

(51) Int. Cl.$^7$ .................. A61K 33/38; A61K 31/19; A61K 31/28; A61K 47/00

(52) U.S. Cl. .................. 424/618; 424/DIG. 6; 424/DIG. 13; 514/495; 514/561; 514/562; 514/564; 514/565; 514/574; 514/784; 514/836; 514/859; 514/912

(58) Field of Search .................. 424/618, DIG. 6, 424/DIG. 13; 514/495, 561, 562, 564, 565, 574, 724, 784, 836, 859, 912

(56) References Cited

U.S. PATENT DOCUMENTS

| | | |
|---|---|---|
| 4,055,655 A | 10/1977 | Maurer et al. |
| 4,915,955 A | 4/1990 | Gömöri |
| 5,322,520 A | 6/1994 | Milder |
| 5,336,508 A | 8/1994 | Marty |
| 5,437,858 A | 8/1995 | Hungerbach et al. |
| 5,785,972 A | 7/1998 | Tyler |
| 5,792,793 A | 8/1998 | Oda et al. |
| 5,824,292 A | 10/1998 | Carr et al. |
| 5,932,251 A | 8/1999 | Kirkpatrick |
| 5,961,843 A | 10/1999 | Hayakawa et al. |
| 6,197,814 B1 | 3/2001 | Arata .................. 514/495 |
| 6,583,176 B2 | 6/2003 | Arata .................. 514/495 |

FOREIGN PATENT DOCUMENTS

| | | |
|---|---|---|
| EP | 0 115 130 A1 | 8/1984 |
| EP | 0 876 762 A1 | 11/1998 |
| FR | 2125505 | 9/1972 |
| GB | 1587671 | 4/1981 |
| WO | WO 99/18790 | 4/1999 |

OTHER PUBLICATIONS

Sanchez et al., Comparative Potentiometric Determination of the Stability Constants of Silver (I) with α–Alanine, DL–Phenylalanine, and DL–Serine, *Analusis*, 9(9): 455–8 (1981).

Poddymov et al., Interaction of Amino Acids with Ag(I) and Hydrogen Ions in Aqueous Solutions, *Zh. Neorg. Khim*, 26(5): 1307–13 (1981).

Poddymov et al., Formation of Complexes Between Ag(I) and Several Amino Acids, *Zh. Neorg. Khim*, 22(6): 1617–20 (1977).

STN/CAS online, file CAPLUS, Acc. No. 1977:459144, (Poddymov et al., Zh. Neorg. Khim. (1977), 22(6), 1617–20), Abstract.

STN/CAS online, file CAPLUS, Acc. No. 1982:12190, (Utrilla Sanchez et al., Analusis (1981), 9(9), 455–8), Abstract.

STN/CAS online, file CAPLUS, Acc. No. 1981:431262, (Poddymov et al., Zh. Neorg. Khim. (1981), 26(5), 1307–13), Abstract.

*Primary Examiner*—S. Mark Clardy
*Assistant Examiner*—Frank Choi

(57) ABSTRACT

The invention relates to a substantially non-colloidal solution made by combining ingredients comprising (a) water; (b) a source of free silver ions; and (c) a substantially non-toxic, substantially thiol-free, substantially water-soluble complexing agent.

30 Claims, No Drawings

IONIC SILVER COMPLEX

CROSS-REFERENCE TO RELATED APPLICATIONS

This application is a continuation of application Ser. No. 10/175,260, filed on Jun. 18, 2002, now abandoned, which is a continuation of application Ser. No. 09/796,242, filed on Feb. 28, 2001, now abandoned, which is a continuation of application Ser. No. 09/435,158, filed Nov. 5, 1999, now abandoned, which claims the benefit of U.S. Provisional Application No. 60/107,710, filed Nov. 9, 1998. Each of the applications is incorporated by reference in their entireties.

BACKGROUND OF THE INVENTION

1. Field of the Invention

This invention relates to solutions including complexed ionic silver. More particularly, it relates to solutions including complexed ionic silver wherein the solutions convey health benefits through their use or application.

2. Description of Related Art

Silver has been known to act antimicrobially as an agent in and on the body of humans as well as other animals, and to be relatively non-toxic to mammalian cells when used in the minute quantities needed to be antimicrobially effective. The most effective form of silver for antimicrobial use is as ions in solution. Silver ions have been shown in the past to have antibacterial, antiviral and antifungal qualities, and to contribute directly to the regeneration of tissue. While the exact method by which silver ions perform these functions is not known, it is believed that they may (1) disrupt the respiratory functions, or (2) disrupt membrane functionality of single-celled microorganisms, or (3) link to the cell's DNA and disrupt cell functions. It is not conventionally understood why silver ions appear to some to be effective at regenerating tissue, which apparently involves more than acting as an antimicrobial agent.

During recent years, ionic silver substances have been undergoing a substantial resurgence in popularity, and are increasingly regarded as a reasonably safe and effective antimicrobial agent. Silver ion substances are increasingly being used in medical applications as well as by those seeking a natural alternative to traditional antibiotic medications. Ionic silver substances are being used in topical dressings to treat wounds and to prevent and treat infections. They are also being used for water supply sanitation for public utilities, for pharmaceutical equipment sanitation, and for killing germs including the germ that causes Legionnaires' Disease in the water systems of hospitals. Tooth brushes are now being introduced that release silver ions in order to fight oral bacteria.

However, delivering silver ions for utilization in or on the body is a challenge because silver ions are electrically attracted to a host of substances in and on the body, resulting in the silver ions rapidly forming complexes or compounds wherein the ion is no longer available to perform the appropriate antimicrobial function. A controlled, gradual release of silver ions is desirable for achieving appropriate use of silver ions in or on the body in order to offset this phenomenon, and is especially challenging for antimicrobial use of silver ions internally such as upon oral ingestion. If free silver, defined as silver ions which are not part of a complex or compound, and are therefore biologically available, are delivered at once to the body, there is only opportunity for them to perform the antimicrobial function for an instant where they make contact with the body or the oral tissue before being rendered inactive.

The desirable characteristics of an antimicrobial ionic silver formulation are that it gradually releases its silver content as free silver ions upon ingestion or upon topical application in a manner that is slow enough to sustain the antimicrobial functionality for a sufficient period of time while also being rapid enough to be substantially effective, that it facilitate mobility of the silver through the body upon oral ingestion prior to gradually releasing its silver content as available free silver ions, and that it be nontoxic to the body.

Topical applications of ionic silver do not require a controlled, gradual release of silver ions to the degree that internal, oral ingestion applications require it because there is a lower presence of agents with which the silver ions can bind up and form complexes or compounds upon topical exposure as compared with ingestion for internal use. At least one product has been recently introduced that consists of a film dressing impregnated with a complex that gradually releases silver ions upon exposure to the body's chemistry.

Previously, some silver-containing chemical substances, such as silver nitrate, have been utilized in an effort to gain the antimicrobial benefits of silver ions, but these substances have proven minimally effective in or on the body because they immediately deliver all of their silver content as free silver ions. Some such substances, such as silver nitrate, are undesirably toxic to the human body when administered in typical doses.

Colloidal silver is a substance which has been in use for about a hundred years. It provides a reasonable degree of controlled release and mobility of silver ions in and on the body. Colloidal silver is apparently made up of minute particles of silver, associated with silver ions that comprise a small percentage of such particles. The mass of these particles provide a degree of controlled, gradual release of silver ions as the body's chemistry breaks down these particles.

However, the electrolysis process that is used to make most colloidal silver has substantial limitations and does not enable adequate consistency in terms of parts per million (PPM) of silver relative to the total solution by molar weight, particle size, or percentage of ions, for most desired applications. Additionally, purity of the substance is typically limited because electrolytes must usually be added to the water during the production method, the most common of which is sodium. Oxides typically form during production, often resulting in an undesirable yellow or brown color. Moreover, the potency of most electrically produced colloidal silver is inherently limited. After a concentration of approximately 5 PPM of silver (in some cases up to approximately 20 PPM of silver) is reached, the production method typically fails to continue yielding electron-deficient silver particles. The particles formed after such a concentration is reached are typically not capable of performing antimicrobial functions as do the particles that are initially produced prior to reaching this approximate level of total silver concentration (the aggregate of the complexed silver and the free, available silver in the water-based solution).

The term colloidal means "something suspended in a dissimilar medium," and shelf life is, therefore, inherently limited because the colloidal silver particles gradually settle out of the water. Colloidal particles are not dissolved in the water medium; they are not in solution. The suspension is a result of, for example, Brownian motion which is insufficient to keep the particles from settling out over time. Some colloidal silver substances have stabilizing agents such as proteins added to the formula, but these tend to further hinder the availability of the silver ions to the body. What is therefore needed are compositions comprising silver ions, and methods of making and using such compositions, that address the aforementioned problems.

SUMMARY OF THE INVENTION

In an aspect, the invention relates to a substantially non-colloidal solution made by combining ingredients comprising (a) water; (b) a source of free silver ions; and (c) a substantially non-toxic, substantially thiol-free, substantially water-soluble complexing agent.

DETAILED DESCRIPTION

The inventors have unexpectedly discovered that a substantially non-colloidal solution made by combining ingredients comprising (a) water; (b) a source of free silver ions; and (c) a substantially non-toxic, substantially thiol-free, substantially water-soluble complexing agent overcomes many of the limitations inherent in the aforementioned forms of ionic silver substances and has wide application in and on the body.

The inventive, substantially non-colloidal solution provides silver ion concentrations well above those typically provided by colloidal silver products. The production method provides a typically consistent formulation. The inventive formulation is highly stable, has many years of shelf life, and maintains its consistency and structure under a wide range of environmental conditions. Substantially wide concentration ranges of complexed silver are attainable without significantly compromising the desirable characteristics of the product. The composition of the invention efficiently provides for substantial mobility of the silver complex through the body and for controlled decomplexing of its silver content, whereupon it gradually releases silver as available free silver ions, upon introduction of the product to the body's chemistry internally through oral ingestion or upon topical application.

Further, the inventive, substantially non-colloidal solution is relatively nontoxic to the human body at typical doses.

The inventive substantially non-colloidal solutions are made from ingredients comprising water, a source of free silver ions; and a substantially non-toxic, substantially thiol-free, substantially water-soluble complexing agent.

Water usable in the practice of this invention should be relatively pure. Suitable types of water include: deionized water, distilled water, reverse osmosis filtered water, reagent grade water and USP grade water suitable for use in pharmaceuticals. The water is desirably substantially free of contaminants, such as parasites, pathogens, chemical contaminants, and particulate contamination.

The source of silver ions may be virtually any compound or complex which includes silver ions as a constituent, from which those silver ions can be obtained in order to be complexed with the recited complexing agent or to become free silver ions as part of the inventive solution. Sources of silver ions comprise silver oxide, trisilver citrate, silver acetate, water soluble silver salts or any number of other sources of silver without departing from the scope of the invention. In a preferable embodiment, the source of silver ions is silver oxide (AgO). On complexing, silver oxide eliminates a superfluous counter ion, hydroxide, which is innocuous since hydroxide is already present in the solution.

The substantially non-toxic, substantially thiol-free, substantially water-soluble complexing agent serves primarily to provide a "controlled release" of biologically active silver ions. In the context of the invention, complexing agent may be taken to mean an ionic material with which silver ions are complexed in such a manner that the complexing agent forms a weak bond with the silver ions wherein the missing electron position which is a characteristic of the silver ion is filled by an electron of the complexing agent. The substantially non-toxic, substantially thiol-free, substantially water-soluble complexing agent may comprise a carboxylic acid, or a primary, secondary or tertiary amine. In the context of this invention, substantially non-toxic may be taken to mean that the recited complexing agent, when present in the inventive solution in usual amounts according to the invention, and when administered as part of the inventive solution in usual dosage amounts of the inventive solution, creates little or no toxic effects in a host to which the inventive solution is administered. In an embodiment, the substantially non-toxic, substantially thiol-free, substantially water-soluble complexing agent comprises amino acids or hydroxy acids. In a preferable embodiment, the amino acids comprise glycine, alanine, valine, leucine, isoleucine, methionine, proline, phenylalanine, tryptophan, serine, threonine, tyrosine, asparagine, glutamine, aspartic acid, glutamic acid, lysine, arginine, or histidine. In another preferable embodiment, the hydroxy acids comprise glycolic acid, lactic acid, malic acid, tartaric acid, citric acid, or mandelic acid. In a more preferable embodiment, the citric acid comprises dibasic citrate. Citrate, a key constituent of the metabolic system, is aggressively drawn to the cells throughout the body and provides an efficient delivery system for spreading the silver through the body before decomplexing takes place and the silver is gradually released as available free silver ions. Also useful are acetic acid; certain crown ethers; primary, secondary or tertiary amines, such as ethanolamine, and other conventionally known substantially non-toxic, substantially thiol-free, substantially watersoluble complexing agents.

In an embodiment, the inventive substantially non-colloidal solution possesses greater than about twenty parts of silver per million parts of the non-colloidal solution. In the context of this invention, PPM is defined as parts of total silver to 1,000,000 parts of the total solution including the water base and all substances contained in it by weight. In another embodiment, the substantially non-colloidal solution possesses greater than about fifty parts of total silver per million parts of the non-colloidal solution. In a more preferable embodiment, the substantially non-colloidal solution posesses greater than or equal to about one hundred parts of total silver per million parts of the non-colloidal solution. Higher parts per million of total silver are desirable, as biological effectiveness increases as PPM free silver increases.

100 PPM of silver is a desirable level for the total concentration of silver because it provides a highly effective concentration of silver yet the concentration is low enough to facilitate ease of measuring and dispensing the small dosages appropriate for small children and small animals. However, the amount of silver can vary substantially, within solubility limits, without departing from the scope of the invention, as long as the other elements are varied in relative proportion to the silver. In another embodiment, the inventive solution may be comprised of as little as about 10 PPM of silver or as much as about 10,000 PPM of silver without departing from the scope of the invention.

In an aspect of the invention, counter ions may be utilized. Such counter ions may be used to balance the charge present in the recited complexing agent, if necessary. Sources for counter ions suitable for use in this invention include those conventionally known sources of counter ions. Any suitable source of counter ions may be used where the complexing agent is such that a counter ion is required to maintain the electrical stability of the silver complex, so long as the counter ion used does not compete with the silver for the complexing agent. In a preferable embodiment, the source of counter-ions comprises alkali metals or alkaline earth metals, such as, potassium ions, or calcium ions.

In an aspect of the invention, the inventive non-colloidal solution possesses less than about ten weight percent of free silver based on the weight of total silver. In an aspect of the invention, the non-colloidal solution possesses less than about one weight percent of free silver based on the weight of total silver. In an aspect of the invention, the non-colloidal solution possesses less than about one-tenth of a weight percent of free silver based on the weight of total silver. A relatively low amount of free silver as compared to total silver (including non-free silver or complexed silver), is retained in a non-reacted state in the inventive solution, until released over time by the equilibrium driving force. This controlled release aspect of the inventive formulation is desirable, as activity is retained over time.

The preferred embodiment of the invention, containing a complex of citrate and silver with potassium as a counter ion, may include the following complex of ions in a solution of relatively pure water:

OOCCH$_2$C(OH)(COO$^-$)CH$_2$COOH (aq).

In a preferable embodiment the inventive solution may be made by mixing silver oxide, citric acid and tripotassium citrate in an approximately 1*4 molar ratio, respectively, in sufficient pure water to produce a silver concentration of 100 parts per million. Other formulations which result in an approximate 1:2 molar ratio to an approximate 1:20 molar ratio of silver to dibasic citrate in no way depart from the scope of the invention. Generally, a preferable molar ratio (as dry ingredient or as solution) of silver to complexing agent is from about 1:1 to about 1:200, more preferably from about 1:1.5 to 1:50, most preferably from about 1:2 to about 1:20.

In another preferable embodiment, the free silver ions are present in the substantially non-colloidal solution in an anti-microbially effective amount.

The inventors have also produced the product following the general procedures described above but reducing the amounts of citric acid and of potassium citrate to half of the amounts described above. Numerous other variations can also be utilized with these starting ingredients provided that the ratio of citric acid to potassium citrate is generally maintained. Likewise, the amount of silver oxide may be substantially increased or decreased provided that a reasonably commensurate adjustment is made in the relative amounts of citric acid and of potassium citrate to silver oxide although, as demonstrated by the fact that the product was successfully produced upon changing the ratio of silver oxide to citric acid and to potassium citrate by 100%, substantial latitude exists with regard to that ratio.

As previously stated herein, numerous alternative source ingredients for yielding the silver ion, complexing agent, and counter ion for the preferred embodiment of the invention may also be used, requiring appropriately adjusted quantities, and, likewise, numerous other complexing agents and, if required, counter ion agents, may be selected as the constituents of the product as well, also requiring the appropriately adjusted quantities of the appropriate source ingredients necessary to produce the desired product.

It has often been claimed that ionic silver can kill over 650 disease-causing germs. The invention is absolutely harmless to the body when used in the low quantities needed for the antimicrobial action to occur, especially since the formulation provides an efficiently controlled, gradual release of free silver ions (provided that the complexing agent is nontoxic), requiring less silver ingestion in order to obtain the benefits of silver ion activity that other substances cannot render with substantially higher levels of silver ingestion.

Ionic silver is used for literally hundreds of conditions, including eye and ear infections, nose, sinus and gum infections, acne, sore throats, colds and flu, candida, bladder and vaginal infections, cuts and burns, many skin conditions, bug bites, fighting nail and skin fungus, healing sunburn, alleviating diaper rash and bed sores, providing a soothing skin treatment after shaving, and use as a mouth rinse. Body odors are caused by bacteria in the perspiration, which is often alleviated upon application of the invention, clearly demonstrating how effectively it kills bacteria. Ionic silver is also used for treating ulcers, both in fighting the bacteria that can aggravate an ulcer and in repairing the damaged stomach lining. Ionic silver is used for many severe conditions as well, including, for example, tuberculosis, Epstein-Barr Virus, Lyme Disease, Legionnaires' Disease, bronchitis, chicken pox, and numerous others. There are actually few germ-related conditions, or conditions requiring the repair of tissue, for which ionic silver is not used, since many claim it is not only effective in killing most bacteria but also many if not most fungus and viruses. Some reports indicate that it is also effective against a number of parasites that might invade the body. Ionic silver is also reported by some researchers to be effective at treating cancer and HIV.

Other uses for ionic silver range from purifying bottled water by placing some in the water, to retardation of food spoilage at home. Recent studies show that over 30 percent of bottled water contains bacteria levels above safety limits, which can readily be addressed with a few drops of the invention being added to the water. Spraying sliced fruits with the formulation of the invention can keep them fresh up to a week before spoilage, clearly demonstrating how effectively the invention kills bacteria on foods. It is also used to reverse existing contamination of foods.

Ionic silver is also considered by many to be very useful in oral irrigation systems designed for consumer use, that spray a fine stream of water in the mouth, in fighting infection and healing gums. Ionic silver is even reputed to be quite effective in facilitating the growth of hair in the local area on which it is topically applied.

In virtually all applications for which ionic silver is used, the advantages of a relatively high PPM of silver, a controlled, gradual release of available free silver ions and, in the case of the preferred embodiment of the invention, the benefit of citrate as a carrier on internal use together with the lack of toxicity and minimum likelihood of incurring mutated strains of germs, all serve to provide substantially superior benefits to those who would use the product for any of the myriad of conditions for which ionic silver would be used.

The product can readily be bottled or packaged with a variety of types of dispensers to further facilitate its usefulness. A bottle with a dropper is most convenient for eye drops, ear drops and nose drops. Alternatively, a plastic squeeze bottle can serve as a convenient dispenser for eye drops and ear drops, while the same with a nasal sprayer feature can readily facilitate use as a sinus and nasal spray. A spray dispenser such as with, for instance, a pump spray, makes it very convenient to apply the product externally and also provides a convenient and efficient method for oral use and internal ingestion. By disbursing the product upon spraying it in the mouth, such a spray facilitates absorption of the formula into the blood system through the tissue lining in the mouth. A spray dispenser also facilitates delivery of the product to the lungs as one may inhale while spraying the product towards the throat area while inhaling. Because of the existence of a weak complex of silver and the existence of available free silver ions, along with the photoreactive qualities of silver, packaging should preferably be in an opaque glass container, in a stainless steel container, or in a polypropylene or polyethylene plastic container. Ideally, dispensers should be made of such materials as well.

Topically applying a gauze, cotton, sheer strip or other type of bandage or fabric that has been saturated with the product is another alternative for using the product.

The product can be used for humans as well as animals. When the complexing agent is a nontoxic material, the product is safe for children and pets. Thus, the invention has a wide range of potential uses for both medical and veterinary applications.

The product can also be applied to surfaces for killing germs thereon. For instance, it can be sprayed on counter tops, cutting boards, toilet seats, doorknobs, telephone handsets, etc. Upon contact with germ cells, the available free silver ions should react with and kill the germ cell, causing another silver ion to be decomplexed and released from the complexing agent and be made available.

The invention may be utilized in both the prevention and the treatment of disease.

Due to the efficient delivery of silver ions afforded by the invention, an individual may ingest the product on a daily basis as a preventative, achieving substantial levels of protection from germs, while remaining within extremely safe limits of daily and lifelong silver intake relative to the amount of silver contained in the product in the preferred embodiment. Studies show that the amount of silver in the average daily diet of adult Americans was depleted by as much as 85% between the early half of the 20th century and the latter part of that century. With the preferred embodiment of the invention, an individual consuming a substantial amount of the product on a daily basis in terms of potential health benefits would, in fact, be consuming no more silver than that amount which was depleted from the diets over that period of time.

EXAMPLES

Example 1

Two and one-half liters of pure water were placed in a 5-gallon (1 9-liter functional capacity) carboy mounted on a magnetic stirrer with a Teflon-coated magnetic stir bar placed inside the carboy, turning on the stirrer at low speed, adding 6.7675 grams of citric acid anhydrous powder (reagent grade), 11.43 grams of potassium citrate monohydrate crystal (reagent grade), and 2.2450 grams of silver oxide powder (reagent grade), stirring at low speed for approximately 45 minutes. Next more water was slowly fed while continuing to stir at low speed for approximately an additional 15 minutes and stopping the water input when the level reaches approximately 8–9 liters. Then, the stir speed was turned to high and stirring continued for approximately an additional 30 minutes, filling the carboy to approximately the 18-liter mark, turning off the stirrer, opening the water input valve and stopping the water input at precisely the 19-liter mark, turning the stirrer back on to the high speed, and stirring for an additional 60 minutes.

Example 2

A 65-year old male developed conjunctivitis and obtained relief within less than five hours upon administering two drops of the solution of Example 1 in his eye.

Example 3

A sixteen-year old female had been suffering with acne for three or four years. A dermatologist had been treating her regularly to no avail. She applied six sprays of the solution of Example 1 three times per day to her face for three days and stopped using products from the dermatologist, and by the end of the third day the skin on her face cleared up almost completely. There was no dryness or redness any more.

Example 4

A 45-year old male had been diagnosed with lymphatic cancer and after taking an oral dose of one teaspoon of the solution of Example 1 per day for two months, tests showed that not a trace of the disease remained.

Example 5

A 31-year old male and a 28-year old male who work together in the same store had both come down with a full-blown flu. Both took fifteen drops of the solution of Example 1 in an oral dose, one time, and within a day-and-a-half both were completely free of any further symptoms.

Example 6

A one-year old male was diagnosed with a blocked tear duct in his left eye. Every day, he awoke with a green drainage that continued through the day. Two physicians recommended surgery. The boys mother administered only one drop of the solution of Example 1 in his eye each day for two days. The condition disappeared. Upon a follow-up nine months later, the condition had not returned.

Example 7

A 53-year old woman burned the back of her hand on a 450-degree oven. The burn was approximately an inch-and-a-quarter in diameter. After a week, it still had not begun to heal. The pain was still so bad that she could barely move her hand. She put two drops of the solution of Example 1 on it. By that same night, it had completely scabbed over and the entire circumference of the burn had already generated new tissue. The pain was completely gone and she had regained complete movement of her hand. Within about four more days of applying the invention, it was completely healed, without any scarring.

Example 8

A 61-year old male had developed a urinary tract infection. A urologist put him on sulfa drugs for twenty days. He suffered through a week of constant nausea, at which point he threw out the remaining pills. He then began to ingest 30 drops of the solution of Example 1 per day, and after three days the infection was no longer detectable.

Example 9

A forty-four-year old male developed abscesses surrounding two wisdom teeth. Three oral surgeons told him the teeth had to come out. He applied approximately one teaspoon of the solution of Example 1 each to each of the two affected areas. By the next day, the infections were undetectable and the pain was gone. A follow-up eleven months later showed that it had not returned.

Example 10

A twenty-four-year old woman developed a vaginal infection. The doctor's prescription didn't help after almost two weeks. She then mixed one half-teaspoon of the solution of Example 1 in pure water and used the mixture as a douche, and the discomfort disappeared almost immediately and had not returned upon a follow-up three weeks later.

What is claimed is:

1. A composition comprising (1) water, (2) a silver complex, wherein the silver complex comprises silver complexed with a complexing agent, and (3) a counter-ion; wherein the composition is a substantially non-colloidal soultion, wherein the complexing agent is substantially non-toxic, substantially thiol-free, and substantially water-soluble and comprises one or more amino acids and/or hydroxy carboxylic acids; wherein the molar ratio of complexing agent to silver is greater than one; wherein the counter-ion comprises one or more alkali metals and/or alkaline earth metals; and wherein the silver concentration does not exceed about 10,000 ppm.

2. The composition of claim 1, wherein the composition possesses less than ten weight percent of free silver based on the weight of total silver.

3. The composition of claim 1, wherein the composition possesses less than one weight percent of free silver based on the weight of total silver.

4. The composition of claim 1, wherein the composition possesses less than one-tenth of a percent by weight of free silver based on the weight of total silver.

5. The composition of claim 1, wherein the molar ratio of silver to complexing agent is 1:1.5 to 1:200.

6. The composition of claim 1, wherein the molar ratio of silver to complexing agent is 1:1.5 to 1:50.

7. The composition of claim 1, wherein the molar ratio of silver to complexing agent is 1:2 to 1:20.

8. The composition of claim 1, wherein when the complexing agent comprises one or more amino acids, the amino acid comprises glycine, alanine, valine, leucine, isoleucine, methionine, proline, phenylalanine, tryptophan, serine, threonine, tyrosine, asparagine, glutamine, aspartic acid, glutamic acid, lysine, arginine, and/or histidine.

9. The composition of claim 1, wherein when the complexing agent comprises one or more hydroxy carboxylic acids, the hydroxy carboxylic acid comprises glycolic acid, lactic acid, malic acid, tartaric acid, citric acid, and/or mandelic acid.

10. The composition of claim 1, wherein the counter-ion comprises potassium and/or calcium.

11. The composition of claim 1, wherein the silver concentration is about 10 ppm of silver to about 10,000 ppm of silver.

12. The composition of claim 1, wherein the silver concentration is about 20 ppm of silver to about 10,000 ppm of silver.

13. The composition of claim 1, wherein the silver concentration is about 50 ppm of silver to about 10,000 ppm of silver.

14. The composition of claim 1, wherein the silver concentration is about 100 ppm of silver to about 10,000 ppm of silver.

15. A composition comprising (1) water, (2) a silver complex, wherein the silver complex comprises silver complexed with citrate, citric acid or a combination thereof, and (3) a counter-ion; wherein the composition is a substantially non-colloidal soultion; wherein the complexing agent is substantially non-toxic, substantially thiol-free, and substantially water-soluble; wherein the molar ratio of complexing agent to silver is greater than one; wherein the counter-ion comprises one or more alkali metals and/or alkaline earth metals; and wherein the silver concentration does not exceed about 10,000 ppm.

16. The composition of claim 15, wherein the citrate comprises dibasic citrate.

17. The composition of claim 15, wherein silver is complexed with citric acid and tripotassium citrate.

18. The composition of claim 15, wherein the composition possesses less than ten weight percent of free silver based on the weight of total silver.

19. The composition of claim 15, wherein the composition possesses less than one weight percent of free silver based on the weight of total silver.

20. The composition of claim 15, wherein the composition possesses less than one-tenth of a percent by weight percent of free silver based on the weight of total silver.

21. The composition of claim 15, wherein the molar ratio of silver to citrate, citric acid, or a combination thereof is 1:1.5 to 1:200.

22. The composition of claim 15, wherein the molar ratio of silver to citrate, citric acid, or a combination thereof is 1:1.5 to 1:50.

23. The composition of claim 15, wherein the molar ratio of silver to citrate, citric acid, or a combination thereof is 1:2 to 1:20.

24. The composition of claim 15, wherein the counter-ion comprises potassium and/or calcium.

25. The composition of claim 15, wherein the silver concentration is about 10 ppm of silver to about 10,000 ppm of silver.

26. The composition of claim 15, wherein the silver concentration is about 20 ppm of silver to about 10,000 ppm of silver.

27. The composition of claim 15, wherein the silver concentration is about 50 ppm of silver to about 10,000 ppm of silver.

28. The composition of claim 15, wherein the silver concentration is about 100 ppm of silver to about 10,000 ppm of silver.

29. The composition of claim 15, wherein the counter-ion comprises potassium and/or calcium.

30. A method for treating a disease or condition in a human subject, comprising administering to a human subject in need thereof an effective amount of the composition of any one of claims 1–29, wherein the disease or condition is selected from the group consisting of conjunctivitis, acne, lymphatic cancer, flu, eye infection, burn, urinary tract infection, gum infection and vaginal infection.

* * * * *